United States Patent [19]

Dunn et al.

[11] Patent Number: 4,589,880
[45] Date of Patent: May 20, 1986

[54] DISPOSABLE SPERMICIDE-RELEASING DIAPHRAGM

[75] Inventors: Richard L. Dunn; Richard N. Terry; Donald R. Cowsar; Robert A. Casper, all of Birmingham, Ala.

[73] Assignee: Southern Research Institute, Birmingham, Ala.

[21] Appl. No.: 513,773

[22] Filed: Jul. 14, 1983

[51] Int. Cl.[4] .................. A61K 9/22; A61F 2/66; A61F 5/46
[52] U.S. Cl. .................. 604/892; 604/55; 604/93; 128/127; 128/130; 128/131; 424/78; 424/DIG. 14
[58] Field of Search ............ 604/890, 892, 55, 93; 128/127, 130, 131; 424/DIG. 14, 78; 264/299

[56] References Cited

U.S. PATENT DOCUMENTS

| | | | |
|---|---|---|---|
| 2,234,495 | 3/1941 | Lay | 128/127 |
| 2,697,057 | 12/1954 | Senger et al. | 154/110 |
| 3,015,598 | 1/1962 | Jones | 156/222 |
| 3,117,575 | 1/1964 | Snell | 128/127 |
| 3,545,439 | 12/1970 | Duncan | 128/260 |
| 3,920,805 | 11/1975 | Roseman | 424/15 |
| 3,975,350 | 8/1976 | Hudgin et al. | 260/30.4 N |
| 3,991,760 | 11/1976 | Drobish et al. | 128/127 |
| 3,995,633 | 12/1976 | Gougeon | 128/260 |
| 4,007,249 | 2/1977 | Erb | 264/222 |
| 4,012,496 | 3/1977 | Schopflin et al. | 424/15 |
| 4,093,490 | 6/1978 | Ziets et al. | 156/245 |
| 4,187,286 | 2/1980 | Marcus | 424/78 |
| 4,198,965 | 4/1980 | Strickman et al. | 128/127 |
| 4,198,976 | 4/1980 | Drobish et al. | 128/260 |
| 4,200,090 | 4/1980 | Drobish | 128/127 |
| 4,219,016 | 8/1980 | Drobish et al. | 128/130 |
| 4,286,587 | 9/1981 | Wong | 128/127 |
| 4,286,593 | 9/1981 | Place et al. | 128/260 |
| 4,292,965 | 10/1981 | Nash et al. | 128/260 |
| 4,304,226 | 12/1981 | Drobish et al. | 128/127 |
| 4,311,543 | 1/1982 | Strickman et al. | 156/224 |
| 4,369,773 | 1/1983 | Chvapil | 128/127 |
| 4,469,671 | 9/1984 | Zimmerman et al. | 424/78 |

OTHER PUBLICATIONS

Lachman et al., *The Theory and Practice of Industrial Pharmacy*, Lea & Febiger, 1976, pp. 32–38.
Proceedings from Drug Delivery Systems Workshop, Baker et al., "Intrauterine Release of Estriol for Contraception, Part II Device Fabrication and In Vitro Release Rates", pp. 49–78, 215–216, Aug. 2–3, 1976, U.S. Dept. Health Education and Welfare, N1H, Bethesda, Md.
"Population Reports Barrier Methods", Series H, No. 4, Jan. 1976, Dept. of Med. and Pub. Aff., GWU Med. Center, Wash., D.C.
"Population Reports Barrier Methods", Series H, No. 5, Sep. 1979, Population Info. Prog., Johns Hopkins U., Baltimore, Md.

Primary Examiner—Morton Foelak
Assistant Examiner—Nathan M. Nutter
Attorney, Agent, or Firm—William H. Needle; Sumner C. Rosenberg

[57] ABSTRACT

A disposable, spermicide-releasing intravaginal contraceptive barrier formed from a homogeneous blend mixture of a thermoplastic polymer, a water-soluble polymer and a spermicide which is released at a controlled rate sufficient to provide contraceptive action for a period of up to 48 hours and methods of making the same.

20 Claims, 2 Drawing Figures

DISPOSABLE SPERMICIDE-RELEASING DIAPHRAGM

The Government has rights in this invention pursuant to Contract No. N01-HD-0-2854 awarded by the Department of Health and Human Services.

BACKGROUND OF THE INVENTION

1. Field of the Invention

This invention relates to an improved intravaginal contraceptive barrier and, more particularly, to a disposable thermoplastic vaginal diaphragm with controlled release of spermicidal agent and method of making the same.

2. Description of the Prior Art

As an intravaginal contraceptive barrier, the diaphragm—usually a soft rubber cup with a reinforced rim that is inserted into the vagina to block access of sperm to the cervix—is an excellent alternative for women who have conditions which do not allow the use of oral contraceptives or IUD or who do not wish to use these methods. Although the diaphragm is usually 100% risk-free and can be a reliable contraceptive for most women, to be effective it must be used properly.

There are generally four (4) types of commercially available diaphragms. The coil-spring diaphragm contains a round, spiral-coiled, metal wire in the rim which is encircled with rubber. This type of diaphragm is particularly suited for women with strong vaginal muscles and a vagina of normal size and contour. The flatspring diaphragm has a flat, metal band in the rim, and it is firmer than the coil-spring type. The archingspring diaphragm combines features of both coil-spring and flatspring diaphragms. A double metal spring in the rim produces strong pressure against the vaginal walls, and it is used primarily by women with poor vaginal muscle tone. Finally, the Matrisalus diaphragm has a strong, flat steel band in the rim which is curved instead of round to place an added lift against the anterior vaginal wall.

Many factors associated with the use of presently available diaphragms have prevented their wide spread use. While the diaphragm acts as a barrier to most sperm, it is not normally held tightly enough in front of the cervix to prevent entirely the passage of all sperm around the rim. Therefore, the device is used in most instances with a spermicidal cream or jelly. The spermicides are often messy and tend to flow out of the vagina. Replenishing the spermicide can be expensive if the diaphragm is used frequently. The use of conventional diaphragms not only interrupts the normal love-making sequence, but it presents problems with maintenance associated with diaphragm washing, drying, powdering, and inspection.

Numerous contraceptive devices have been developed to eliminate the disadvantages of current reusable diaphragms. Prior art annular devices provide controlled release of surfactant-type spermicides in the vagina, but they do not act as a barrier to sperm deposition on or in the area of the cervix. Devices with compartments that substantially cap or block the cervix and provide controlled release of spermicidal surfactants have been disclosed; however, these devices are not disposable, and they are designed to remain in the vagina and release spermicide during the time between menstrual periods. Because of this length of use, they may develop problems with odor or discomfort, and they are less suited for women who engage in sexual intercourse infrequently.

SUMMARY OF THE INVENTION

The above disadvantages of the prior art are overcome by the present invention which is a disposable, thermoplastic, elastomeric vaginal diaphragm with a controlled release of spermicide. The diaphragm acts as a physical barrier to most sperm, the incorporated spermicide increases contraceptive efficacy and acceptability, and polyethylene glycol, one of the ingredients, provides the required surface lubricity for ease of insertion. It is understood that while the term "diaphragm" is used herein, the present invention is also applicable to other intravaginal contraceptive barriers, such as the cervical cap, vimule and vault cap. It is also understood that while spermicides are the preferred biologically active agents delivered to the vagina, other agents such as antimicrobials or antifungals could also be released from the devices disclosed herein.

The diaphragm is formed from a homogenous blend of a water-soluble polymer, a spermicide, and a thermoplastic elastomer that is biologically compatible. The preferred combination of ingredients for the diaphragm includes Nonoxynol-9 as the spermicide, Estane 5714 from B. F. Goodrich as the thermoplastic elastomer, and polyethylene glycol as the water-soluble polymer. By means of spermicide and polyethylene glycol loading, film thickness and diaphragm area, Nonoxynol-9 is released from the diaphragm through a diffusion mechanism at a controlled rate to provide contraceptive efficacy initially and for 24 hours.

Because of its thermoplastic characteristics, the diaphragm can be made by two methods: dip-coating and melt formation.

DETAILED DESCRIPTION OF THE ILLUSTRATIVE EMBODIMENT

Figure 1:
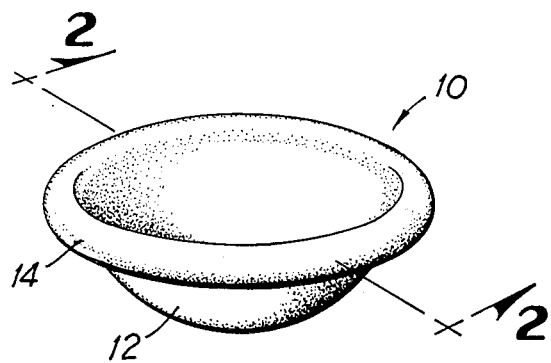
FIG. 1 is a perspective view of the diaphragm of the present invention.
Figure 2:
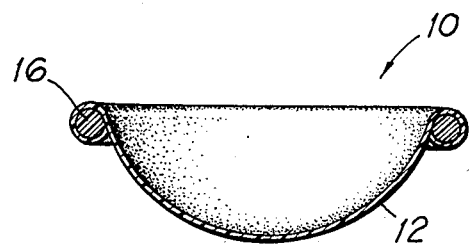
FIG. 2 is a vertical side view of the diaphragm taken along line 2—2 in FIG. 1.

The present invention encompasses disposable devices whose construction allows them to be positioned within the vagina such that they substantially block the access of the sperm to the cervix and provide controlled release of a spermicide or other biologically active agents by diffusion from the device. As seen in FIGS. 1 and 2, the preferred embodiment of this device is that of an imperforate, dome-shaped diaphragm (10) constructed of a thin elastomeric film (12) supported along its rim or outer periphery (14) by a resilient polymeric ring (16). The diaphragm is preferably composed of a biologically compatible, thermoplastic elastomer, such as a polyether-polyurethane, that has been blended homogeneously with a spermicide, such as Nonoxynol-9 (NN9), and a water-soluble polymer, such as polyethylene glycol. The spermicide and the water-soluble polymer migrate to the surface of the device by diffusion, and are released into the vagina at a controlled rate upon contact with vaginal fluid.

The spermicide and water-soluble polymer may be incorporated into either the ring or the dome-like film portion of the device, with the preferred device having a ring and film portion of the same composition. Devices having spermicide uniformly distributed throughout their structure provide a unique and highly effective method of spermicide delivery in the vagina. Spermicide is released (1) from the outer surface of the dome directly on the surface of the ejaculation, (2) from the rim of the device to prevent sperm migration around the rim, and (3) from the inner surface of the dome into the area surrounding the cervix for maximum protection against sperm migration into the cervical os. When a low molecular weight, water-soluble polymer, such as poly ethylene glycol is incorporated along with Nonoxynol-9 into a device made of a polyether-polyurethane elastomer, such as Estane 5714, it migrates to the surface of the device and provides a lubricating film which aids in the insertion of the device into the vagina. The incorporation of the polyethylene glycol also increases the initial amount of spermicide released into the vagina immediately following insertion by aiding in the diffusion of the spermicide. Thus, the rapid initial release of spermicide from the device upon insertion provides effective spermicidal action in the event of coitus immediately following insertion of the device.

The diaphragms of the preferred embodiment will contain and release a sufficient quantity of Nonoxynol-9 at a suitable rate to provide effective spermicidal action immediately and for 24 hours following insertion, even in the event of consecutive coital acts. It is understood that while the perferred period of use is 24 hours, devices of the present invention may be designed to deliver spermicides in the vagina for much longer or shorter periods of use.

Because the subject devices are fabricated from inexpensive, thermoplastic polymers, they may be manufactured in mass quantities at a low cost by standard methods, such as injection-molding and dip-casting. As a result of their low cost, devices of this invention can be made available to a large segment of the population.

The devices disclosed herein, and especially the vaginal diaphragm composed of a thermoplastic elastomer and containing uniformly distributed Nonoxynol-9 and polyethylene glycol, overcome many of the disadvantages of devices of the prior art. Diaphragms encompassed by the present invention eliminate the mess associated with use of accessory spermicides necessary with the current reusable diaphragms. They are more convenient to use because they are disposable and, therefore, require no care and maintenance. They provide effective contraception immediately and for 24 hours following insertion, allowing the user to utilize the product with confidence of efficacy at any time within this period and thus eliminating the proximal timing needed with other vaginal contraceptives. They contain and release sufficient spermicide to provide effective contraception in the event of consecutive coital episodes, and they are relatively inexpensive to use. The aforesaid advantages of the diaphragms disclosed herein should result in a wider user acceptance of products of this nature.

The devices disclosed herein are prepared from components which are described in detail hereinafter.

A. Elastomer

The devices of the present invention are composed of a thermoplastic elastomer containing, as a homogeneous blend, a spermicide and, in the preferred case, a low molecular weight, water-soluble polymer. The thermoplastic elastomers used for the purpose of this invention are vaginally compatible and permeable to the drug to be delivered. As used herein, the word "compatible" means that the polymer does not break down or absorb fluids in the environment of the vagina such that there is a substantial loss of mechanical properties, nor is there absorption of any of the polymeric material itself. Also, the term "compatible" means that there is no deleterious action on the sensitive tissue in the area of the vaginal tract and that the elastomer does not harm the drugs and polymers blended within.

Any compatible, thermoplastic elastomer with suitable drug permeability may be used to prepare the devices of this invention. However, in order to achieve a certain degree of softness and flexibility for the dome and resilience for the ring, it is preferred to use thermoplastic elastomers having an average Shore A hardness of about 40 to 90. The most preferred range is from about 60 to 90. Another major functional parameter of the candidate polymers or elastomers is their mechanical properties. Based upon the mechanical properties of commercial diaphragm materials, the preferred polymer should have a tensile strength of at least 1500 psi and a 100% modulus of at least 100 when loaded with the necessary amount of spermicide and other additives. High molecular weights and high softening points are desirable for good barrier strength and ring resiliency at body temperature (37° C.).

The preferred thermoplastic elastomers are polyurethanes having a polyether or polyester linkage. The most preferrd thermoplastic elastomer is Estane 5714, a polyether based polyurethane made by B. F. Goodrich, Cinncinanti, Ohio. Estane was selected as a material for the diaphragm based on its excellent physical and mechanical properties, as well as its low cost and good processability. Estane is also nontoxic, nonabsorbable, biocompatible and has the drug permeability necessary for the desired release of spermicide. The percentage of Estane in the diaphragm would be 100 minus the percentage of Nonoxynol-9 and water-soluble polymer discussed below.

Other candidate polymers include but are not limited to other polyether-polyurethane block copolymers (e.g., Pellethane), polyurethanes (e.g., Biomer), styrene-butadiene block copolymers (e.g., Kraton), poly(ethylene-co-vinyl acetate) (e.g., Vynathene), polyesters, polyethylene, Nylon, Teflon and the like. Additional thermoplastic materials which are vaginally compatible and which can be utilized in this invention are set forth in U.S. Pat. No. 4,286,587, issued to Wong on Sept. 1, 1981. Although the aforementioned materials are the preferred ones for devices of this invention, the use of other thermoplastic polymers or combinations thereof which have suitable mechanical properties and drug permeability is fully contemplated by this invention.

B. Spermicide

A wide variety of spermicides may be used for the present invention to kill, immobilize or otherwise render sperm cells inactive in the vagina. The most preferred spermicide for use in this invention is Nonoxynol-9, nonylphenoxypolyethoxyethanol, which is currently the most widely used spermicide in vaginal preparations in the United States. Other spermicides which may be used are, for example, p-diisobutylphenoxypolyethoxyethanol (Octoxynol), p-methanylphenyl polyoxyethylene (8.8) ether (Menfegol), dodecamethylene glycol monolaurate, and sodium lauryl sulfate, although any compatible, water-soluble spermicide may be used. Nonoxynol-9 is preferred because it is considered safe and efficacious. GAF Corporation makes Nonoxynol-9 under the trade name of Igepal CO-630. Monsanto also sells Nonoxynol-9 under the trade name of Sterox-NJ. There are also other manufacturers of the spermicide.

The amount of spermicide contained in the devices of this invention vary in accordance with their rate of release from the device and their spermicidal efficacy. In the preferred embodiment of this invention, comprising a diaphragm composed of Estane 5714F-1, Nonoxynol-9 spermicide, and polyethylene glycol, the amount of Nonoxynol-9 used may vary from 3-30% based on the total weight of the device, with the preferred amount in the range of from 5-15% by weight. Based on the amount of Nonoxynol-9 used in vaginal formulations of the prior art and on the estimated concentration of Nonoxynol-9 necessary to immobilize sperm in vaginal fluid, it is desired that devices of the preferred embodiment release approximately 40mg of Nonoxynol-9 within the first hour and from 100-150 mg within 24 hours following insertion into the vagina. Diaphragms preferred by this invention containing approximately 9% by weight of Nonoxynol-9 release the aforementioned desired amount of Nonoxynol-9.

C. Water-Soluble Polymer

With regard to the water-soluble polymer, a waxy, low-molecular-weight compound is preferred for the invention, because it migrates to the surface of the device and provides lubrication on contact with the body without being considered "messy". Accordingly, the waxes should melt near or below body temperature to provide the desired lubrication. The incorporation of a water-soluble, low molecular weight polymer also modifies the release rate of spermicide from the device by providing additional pathways for diffusion as it is released.

The preferred polymer for this invention is polyethylene glycol which has a molecular weight ranging from 600 to 6,000. The most preferred molecular weight of the polyethylene glycol is about 1450. This polymer migrates to the surface of diaphragms composed of Estane 5714F-1 containing 9% by weight of Nonoxynol-9 to form a lubricating film, and modifies the Nonoxynol-9 released by increasing both the overall release rate and the amount of Nonoxynol-9 released initially. The increased initial release of Nonoxynol-9 from the subject diaphragm results in improved efficacy in the event of coitus immediately following insertion of the diaphragm.

Surface coating of the spermicide, by itself or in combination with a low molecular weight, water-soluble polymer, such as polyethylene glycol, may also be used to impart the desirable features aforementioned in reference to the incorporation of the polymers into the devices of this invention.

The preferred range of polyethylene glycol incorporation into the Estane 5714F-1 diaphragms of the preferred embodiment is from 0 to 25% based on total weight of the device. The preferred amount of polyethylene glycol with an average molecular weight of 1450 incorporated into Estane 5714F-1 diaphragms containing 9% by weight Nonoxynol-9 is about 10 to 15% by weight.

D. Spermicide Release Mechanism

The release of Nonoxynol-9 from devices of this invention were characterized by both invitro and in vivo methods. The following in vitro method was utilized to estimate the compositions that would produce the desired Nonoxynol-9 release profile of approximately 40 mg of Nonoxynol-9 within the first hour and from about 100 to 150 mg within 24 hours. Briefly, the in vitro release of Nonoxynol-9 is determined by placing subject samples or devices in an aqueous medium such as distilled water or saline solution, equilibrating the solutions in a 37° C. bath, and sampling the solution at regular time intervals. The samples are analyzed by ultraviolet spectrophotometry and the Nonoxynol-9 concentration in each sample is determined from a standard Beer's law calibration plot of absorbance at a suitable wavelength versus Nonoxynol-9 concentration. If polyethylene glycol is used as the water-soluble polymer, it does not produce any interfering absorption, and the analysis is straightforward. A plot of the Nonoxynol-9 concentration as the ordinate and time as the abscissa describes the release of the Nonoxynol-9 from subject devices with time.

The release of biologically active agents from devices of this invention is characterized by first-order release kinetics as described by Fick's law. If film samples of known geometry are used for analysis, the permeability of an agent dissolved or dispersed in the polymeric film may be determined from the following form of Fick's law for release of dispersed drug from a slab:

$$\frac{C_o l^2}{8} \left[ \frac{M_t}{M_\infty} \right]^2 = (D \cdot C_s) \cdot t$$

where $C_o$=drug loading, $l$=film thickness, $M_t$=mass of agent released at time t, $M_\infty$=mass of agent released at time $\infty$, and t=time. By plotting $$\frac{C_o l^2}{8} \left[ \frac{M_t}{M_\infty} \right]^2$$

as the ordinate and time as the abscissa, the permeability product, $D.C_s$, can be determined as the slope of the initial straight portion of the curve. The permeability product can be then used to determine the drug loading, $C_o$, necessary to produce the desired release of agent.

Based on the foregoing determinations, agent/polymer combinations can be selected which will provide the desired rate of agent release from the preferred devices of this invention. For spermicidal agents having a spermicidal activity similar to Nonoxynol-9, preferred devices would have an agent permeability, $D.C_s$, in the range of $10^{-10}$ to $10^{-12}$ g/cm.sec, and, preferably, about $10^{-11}$ g/cm.sec.

The release of Nonoxynol-9 in vivo from diaphragms of the preferred embodiment of this invention, i.e. Estane 5714F-1 diaphragms containing 9% by weight of Nonoxynol-9 and 14% by weight of polyethylene glycol, (mol. wt. 1450), was determined in baboons by the following method. Nonoxynol-9 with [$^{14}$C] was incorporated into said diaphragms at a level of 0.068% of the Nonoxynol-9 weight. The devices were placed in the vaginas of baboons, removed after specific lenghts of time, and the amount of Nonoxynol-9 remaining in the diaphragms was determined by liquid scintillation counting. The amount of Nonoxynol-9 released during a given test period was then determined from the difference between initial diaphragm loading and the amount of nonoxynol-9 remaining in the diaphragm after the in vivo incubation. Although specific analytical procedures may vary, the methods of in vitro and in vivo analysis of Nonoxynol-9 release from subject devices should have a broad application to include a variety of other agents having biological activity.

E. Method of Manufacture

The following describes an improved method of manufacturing vaginal diaphragms, the preferred devices of this invention, from thermoplastic polymers and elastomers. While the description relates to a preferred and convenient method of manufacture, various other methods can be employed to fabricate said diaphragms and other devices encompassed by this invention.

The first step in the fabrication procedure involves mixing the components of the diaphragm into a homogeneous blend. This may be accomplished by mixing or dissolving the components in a suitable solvent, such as tetrahydrofuran, or by blending the components at elevated temperatures by techniques known to the art. The blended material is then dried thoroughly to remove solvent or moisture, and injection molded into the article described hereinafter.

Methods of fabricating vaginal diaphragms from thermoplastic elastomers are known to the prior art. U.S. Pat. No. 2,697,057, discloses a method whereby disposable diaphragms are manufactured by positioning a thin sheet of thermoplastic material over a circular ring formed by extrusion, and mechanically deforming the thin sheet into the shape of a dome at elevated temperatures, producing the diaphragm barrier and sealing it to the ring. U.S. Pat. No. 4,093,490 discloses an improved method of forming diaphragm rings by injection molding and include the use of vacuum or pressure at elevated temperature to form the diaphragm barrier from a separate sheet of material and to seal it to the ring.

Although the above method can be used to produce the devices disclosed by this invention, the preferred method of diaphragm manufacture disclosed herein is an improved method over the prior art by its elimination of the separate fabrication of sheets of material for the diaphragm barrier, and the sealing of said sheets onto the diaphragm ring. According to the preferred method of this invention, the diaphragm rim is injection molded in a single step with a thin, planar film occluding its center. For brevity, the term "prediaphragm" will be used herein to describe this device. The dome-shaped portion of the diaphragm is formed by deforming the center film portion of the injection molded prediaphragm into a dome-shaped mold by pressure, vacuum or mechanical means at elevated temperatures.

The specific fabrication procedure involves heating the preferred material to a temperature high enough to soften it but low enough to prevent degradation or chemical reaction of any components of the material. The specific heating temperature employed will vary depending upon the composition of the material. For Estane 5714F-1 containing 9% by weight Nonoxynol-9 and 14% by weight polyethylene glycol, (mol. wt. 1450), the injection molding temperature may vary from 135°–150° C. After injection molding, the flash is trimmed from the prediaphragm and it is placed into the annular groove of the diaphragm mold used to form the dome. The prediaphragm is then heated by any suitable method to soften it prior to deforming it into the mold. The preferred method of forming the dome is to apply pressure or vacuum to the softened prediaphragm.

Although the method of manufacture described hereinabove is highly preferred for the diaphragms disclosed by this invention, other methods known to the art can be employed to fabricate diaphragms or other devices encompassed by this invention. For example, devices can be fabricated by a dip-casting process whereby a suitable mandrel, such as a glass tube, is dipped consecutively into a solution of the desired components in a volatile organic solvent. When the desired film thickness has been deposited on the glass tube, and before the film has dried completely, the film is rolled down the tube to the tip and allowed to dry there to form the rim of the device. Devices fabricated by this procedure are then dried thoroughly to remove any trace of solvent.

The resiliency, quality and dimensions of diaphragms produced by dip-coating are subject to many variables within the process. The number of dips and the polymer concentration in solution determine the barrier thickness. The cumulative depth of dipping, the dip sequence, and the rate of removal from solution determine the size and resiliency of the ring.

The following dipping procedure has been established for diaphragms sized for testing in baboons:

Diaphragms with an overall diameter of 44.2 mm and an average barrier thickness of 0.203 mm, ring diameter of 4.32 mm, and barrier depth of 16.51 mm are produced by dipping 33-mm-diameter glass tubes four times to depths of 10, 9, 8, and 7 cm, and allowing the film to dry in between dips. The tubes are removed slowly from the solution and inverted after dipping to dry. The film is then rolled down the glass tube to the tip, where it is allowed to air dry for 24 hours. The diaphragm is then removed and dried in a vacuum oven for 24 hours.

F. Testing

The diaphragms of the present invention have been evaluated in vivo in baboon and rabbits. The in vivo release, migration to the cervix and uterus, and vaginal absorption and excretion of NN9 has been demonstrated utilizing liquid scintillation counting (LSC) analysis.

Efficacy studies in baboon have also shown that control diaphragms were an effective contraceptive only when proper placement in the vagina was retained, whereas the NN9-loaded diaphragms, as a result of their spermicidal activity, were almost always effective even when expelled during coitus. Additionally, none of the diaphragms tested produced any signs of vaginal irritation.

The diaphragm of the present invention could be utilized to deliver other medicaments at a controlled rate. These drugs could include steroids to improve contraceptive efficacy and antimicrobials to treat or control vaginal and related infections such as gonorrhea, herpes, etc. The vaginal diaphragm can also be used to deliver other drugs including antibiotics, antitumor agents, cardiovascular drugs, etc. If other drugs are incorporated within the diaphragm, it could be of a different composition from the spermicide-releasing diaphragm of the present invention. Estane could still be used, but the other ingredients would probably change.

What we claim is:

1. A disposable, spermicide-releasing intravaginal contraceptive device comprising an imperforate, flexible barrier portion having resilient means at an outer periphery, said device formed from a homogeneous blend of effective amounts of a thermoplastic elastomer having an average Shore A hardness of from 40 to 90 and a spermicide whereby, when said device is positioned within the vagina, said spermicide is released by diffusin into the vagina at a controled rate to provide effective spermicidal action for a predetermined amount of time, said device having a first-order release of said spermicide.

2. A device as claimed in claim 1 wherein said elastomer is a polyurethane.

3. A device as claimed in claim 1 wherein said elastomer is Estane 5714.

4. A device as claimed in claim 1 wherein said spermicide is Nonoxynol-9.

5. A device as claimed in claim 1 wherein said homogeneous blend includes an effective amount of a water-soluble polymer.

6. A device as claimed in claim 5 wherein said polymer has a molecular weight ranging from 600 to 6,000.

7. A device as claimed in claim 5 wherein said polymer is polyethylene glycol.

8. A device as claimed in claim 5 wherein said effective amount of spermicide ranges from 3–30% by weight, said effective amount of water soluble polymer ranges up to 25% by weight and said effective amount of elastomer is 100% by weight minus the effective amounts of said spermicide and said polymer.

9. A device as claimed in either claim 1 or claim 5 wherein said ring portion is formed from said homogeneous blend.

10. A device as claimed in claim 1 wherein said device is a vaginal diaphragm.

11. A device as claimed in claim 1 wherein said device is a cervical cap.

12. A disposable, spermicide-releasing intravaginal contraceptive device, comprising a barrier portion formed from a homogeneous blend of effective amounts of Estane 5714, a spermicide and a water-soluble polymer having a molecular weight ranging from 600 to 6,000, said device having a first-order release by diffusion of said spermicide.

13. A method for preventing conception, comprising the step of positioning within the vagina cavity posterior to the introitus and adjacent to the cervical os, prior to coitus, a disposable, spermicide-releasing contraceptive barrier comprised of a homogeneous blend of effective amounts of a thermoplastic, polyether-polyurethane elastomer and a spermicide so that said spermicide diffuses from said barrier for a predetermined amount of time into the area adjacent to the cervical os to provide a spermicidal effect, said barrier having a first-order release of said spermicide by diffusion.

14. A method of manufacturing a disposable vaginal barrier which has a first-order release of spermicide by diffusion through said barrier, comprising the steps of:
(a) mixing together effective amounts of a thermoplasic elastomer and a spermicide to form a homogeneous blend;
(b) shaping said blend into a device having a thin film occluding the center thereof and a resilient rim about its outer periphery; and
(c) forming said film into a dome shape.

15. A method as claimed in claim 14 wherein said elastomer is Estane 5714.

16. A method as claimed in claim 14 wherein said spermicide is Nonoxynol-9.

17. A method as claimed in claim 14 wherein said blend further includes a water-soluble polymer having a molecular weight ranging from 600 to 6,000.

18. A method of fabricating a disposable, vaginal barrier having a first-order release of spermicide by diffusion through said barrier, comprising the steps of:
(a) mixing together effective amounts of a thermoplastic polyether-polyurethane elastomer, a spermicide and a water-soluble polymer having a molecular weight ranging from 600 to 6,000 to form a mixture;
(b) injection molding said mixture at a temperature high enough to soften said mixture but low enough to prevent degradation of any of said elastomer, said spermicide or said polymer so as to form a prediaphragm;
(c) placing said prediaphragm in a mold of desired configuration for said barrier;
(d) softening said prediaphragm;
(e) deforming said prediaphragm within said mold to form said barrier; and
(f) removing said barrier from said mold.

19. A method of fabricating a unitary disposable, spermicide releasing vaginal diaphragm having an imperforate, flexible barrier portion with an outer periphery and a resilient ring portion connected to said outer periphery, comprising the steps of:
(a) mixing together effective amounts of a thermoplastic polyether-polyurethane elastomer, a spermicide and a water-soluble polymer having a molecular weight ranging from 600 to 6,000 to form a mixture;
(b) dipping a tube into said mixture a predetermined number of times to form a film thereon, each successive time said tube being dipped to a more shallow depth within said mixture;
(c) drying said dipped tube between said dippings;
(d) rolling said film a predetermined length down said tube to form said resilient ring portion;
(e) removing said barrier portion and said resilient ring portion from said tube; and
(f) drying said barrier portion and resilient ring portion.

20. A disposable spermicide-releasing intravaginal contraceptive device, comprising a blend of effective amounts of a hydrophobic thermoplastic, polyether-polyurethane elastomer, a spermicide and a water-soluble polymer whereby a matrix is formed that has a first-order rate of release of said spermicide by diffusion.

* * * * *